United States Patent [19]

Wriede et al.

[11] Patent Number: 5,211,737
[45] Date of Patent: May 18, 1993

[54] 4-ARRYL-2-HALOIMIDAZOLE-5-CARBOXY-LIC ESTERS, THE PREPARATION AND USE THEREOF

[75] Inventors: Ulrich Wriede, Mutterstadt; Gerhard Hamprecht, Weinheim; Hermann Koehler, Bobenheim; Thomas Kuekenhoehner, Frankenthal; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 666,483

[22] Filed: Mar. 6, 1991

Related U.S. Application Data

[62] Division of Ser. No. 470,130, Jan. 25, 1990, abandoned.

[51] Int. Cl.[5] .............. A01N 43/50; A01N 35/06
[52] U.S. Cl. .................................................. 504/106
[58] Field of Search ................... 71/92, 98, 97, 123

[56] References Cited

U.S. PATENT DOCUMENTS

| | | | |
|---|---|---|---|
| 3,950,420 | 4/1976 | Sawaki et al. | 71/88 |
| 4,249,937 | 2/1981 | Iwataki et al. | 71/97 |
| 4,440,566 | 4/1984 | Luo | 71/98 |
| 4,578,106 | 3/1986 | Leone-Bay et al. | 71/92 |
| 4,591,377 | 5/1986 | Leone-Bay et al. | 71/92 |
| 4,595,400 | 6/1986 | Leone-Bay et al. | 548/337 |
| 4,639,266 | 1/1987 | Heubach et al. | 71/92 |
| 4,711,962 | 12/1987 | Leon-Bay | 548/337 |
| 4,717,418 | 1/1988 | Warner et al. | 71/98 |
| 4,755,213 | 7/1988 | Schmierer et al. | 71/92 |
| 4,808,213 | 2/1989 | Schmierer et al. | 71/92 |
| 4,830,660 | 5/1989 | Yamamoto et al. | 71/92 |
| 4,995,898 | 2/1991 | Nasu et al. | 71/90 |

FOREIGN PATENT DOCUMENTS 0127446 12/1984 European Pat. Off. .
0180787  5/1986 European Pat. Off. .

OTHER PUBLICATIONS

Leone-Bay, A., *Chemical Abstracts*, vol. 108, 131677x, 1988.

Leone-Bay et al. I "An efficient method ..." Synthetic Communication, 17(12), 1409–1412 (1987).

Primary Examiner—Richard L. Raymond
Assistant Examiner—B. Bembenick
Attorney, Agent, or Firm—Keil & Weinkauf

[57] ABSTRACT

4-Aryl-2-haloimidazole-5-carboxylic esters of the general formula Ia and Ib

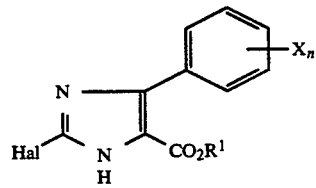

Ia

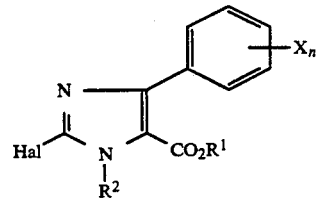

Ib where
$R^1$ is $C_1$–$C_6$-alkyl, $C_3$–$C_6$-alkenyl or $C_3$–$C_6$-alkynyl,
$R_2$ is $C_1$–$C_6$-alkyl, $C_3$–$C_6$-alkenyl or $C_3$–$C_6$-alkynyl,
Hal is chlorine or bromine,
n is 0 to 3,
x is $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylsulfinyl, $C_1$–$C_4$-alkylsulfonyl, $C_1$–$C_4$-haloalkylthio, cyano, nitro, carbo-$C_1$–$C_4$-alkoxy, N,N-di-$C_1$–$C_4$-alkylcarbamoyl and/or halogen, processes for their manufacture, and their use in herbicidal agents as safeners in combination with at least one herbicidal active ingredient from the group consisting of
a) 2-(4-heteroaryloxy)- or 2-(4-aryloxy)-phenoxyacetic acid or -propionic acid derivatives and
b) cyclohexenone derivatives.

11 Claims, No Drawings

4-ARRYL-2-HALOIMIDAZOLE-5-CARBOXYLIC ESTERS, THE PREPARATION AND USE THEREOF

This application is a division of application Ser. No. 07/470,130, filed on Jan. 25, 1990 (abandoned).

The present invention relates to 4-aryl-2-haloimidazole-5-carboxylic esters of the general formulae Ia and Ib

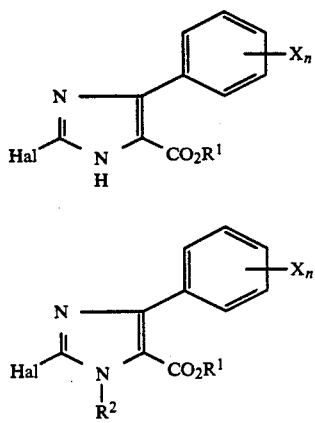

where
$R^1$ is $C_1$–$C_6$-alkyl, $C_3$–$C_6$-alkenyl or $C_3$–$C_6$-alkynyl,
$R^2$ is $C_1$–$C_6$-alkyl, $C_3$–$C_6$-alkenyl or $C_3$–$C_6$-alkynyl,
Hal is chlorine or bromine,
n is 0 to 3,
X is $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylsulfinyl, $C_1$–$C_4$-alkylsulfonyl, $C_1$–$C_4$-haloalkylthio, cyano, nitro, carbo-$C_1$–$C_4$-alkoxy, N,N-di-$C_1$–$C_4$-alkylcarbamoyl and/or halogen.

The present invention also relates to processes for the preparation of the compounds Ia and Ib and to herbicidal agents which contain 2-(4-heteroaryloxy)- or 2-(4-aryloxy)-phenoxyacetic or -propionic and derivatives and/or cyclohexenone derivatives as herbicidal ingredients and arylhaloimidazole derivatives as antidotes, and to methods for the selective control of undesired plant growth using these herbicidal agents.

EP-A-174,562 discloses 1-aryltriazolecarboxylic acid derivatives with a crop-protecting action. There have also been descriptions of 1-arylimidazolecarboxylic esters with growth-regulating properties (EP-A-243,615, EP-A-264,577) and 2-haloimidazolecarboxylic esters with herbicidal actions (EP-A-127,446; EP-A-180,787; U.S. Pat. Nos. 4,711,962; 4,591,377 and 4,578,106).

Herbicidal ingredients from the group of 2-(4-heteroaryloxy)-or 2-(4-aryloxy)-phenoxyacetic acid derivatives of the formula IX

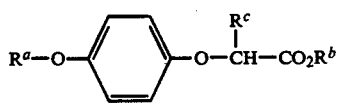

where
$R^a$ is phenyl, pyridyl, benzoxazolyl, benzothiazolyl or benzopyrazinyl, it being possible for these aromatic ring systems to carry up to two of the following: halogen, nitro, $C_1$–$C_4$-alkyl, $C_1$–$C_4$-haloalkyl and/or $C_1$–$C_4$-haloalkoxy, $R^b$ is hydrogen, $C_1$–$C_5$-alkyl, $C_3$–$C_5$-alkylideneimino, $C_3$–$C_5$-alkylideneiminooxy-$C_2$–$C_3$-alkyl or the equivalent of a cation which is tolerated by plants, and $R^c$ is hydrogen or methyl, are used to control undesired plants from the family of Gramineae (e.g. DE-A-2,223,894, DE-A-2,433,067, DE-A-2,576,251, DE-A-3,004,770, BE-A-868,875 and BE-A-858,618). However, the tolerability of these substances for crop plants varies between commercially acceptable and not tolerable, depending on the substituents and application rate.

Similar is true of cyclohexenone derivatives of the formula X

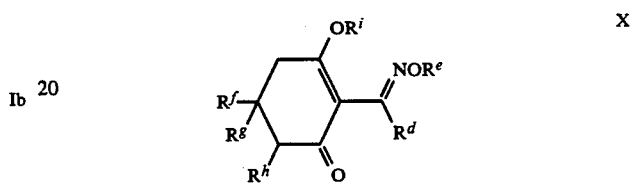

where
$R^d$ is $C_1$–$C_4$-alkyl;
$R^e$ is $C_1$–$C_4$-alkyl, $C_3$–$C_4$-alkenyl, $C_3$–$C_4$-alkynyl, $C_3$–$C_4$-haloalkenyl, or thenyl which can be substituted once by halogen;
$R^f$ is $C_1$–$C_4$-alkyl which can be substituted once by $C_1$–$C_4$-alkylthio or $C_1$–$C_4$-alkoxy; a 5- or 6-membered saturated or singly unsaturated ring system which, besides carbon members, can contain one oxygen, one sulfur or a sulfoxide or sulfone group, and which can carry up to three of the following: hydroxyl, halogen, $C_1$–$C_4$-alkyl, $C_1$–$C_4$-haloalkyl, $C_1$–$C_4$-alkoxy and/or $C_1$–$C_4$-alkylthio; a 10-membered saturated or singly unsaturated heterocycle which contains two oxygens or sulfurs and can be substituted by up to three $C_1$–$C_4$-alkyl and/or methoxy groups; phenyl, pyridyl or isoxazolyl, it being possible for these to carry up to three of the following: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino, $R^g$ is hydrogen, hydroxyl or, if $R^f$ is $C_1$–$C_6$-alkyl, a $C_1$–$C_6$-alkyl group;

$R^h$ is hydrogen, cyano, halogen or $C_1$–$C_4$-alkoxycarbonyl, and $R^i$ is hydrogen or the equivalent of an environmentally compatible cation.

They have likewise been described as herbicides (e.g. EP-A-228,598, EP-A-230,235, EP-A-238,021, U.S. Pat. No. 4,432,786, DE-A-2,439,104) and are mainly used for controlling undesired grasses in dicotyledonous crops and in grasses not belonging to the family of Gramineae. Depending on the structure of the substituents and the dose applied, compounds from this group can also be employed for selective control of undesired grasses in Gramineae crops such as wheat and rice.

The object of the invention is to provide compounds in which the disadvantages associated with the use of the above-mentioned herbicides of the formulae IX and X have been eliminated or at least diminished to such an extent that the reduction in the harvest yield of the crop plants is now zero or negligible.

In accordance with the object, we have found the 1-aryl- and 1-heteroarylimidazolecarboxylic esters Ia and Ib defined in the introduction. We have also found processes for preparing these compounds Ia and Ib and for using these compounds together with the herbicides IX and X for influencing undesired plant growth. The invention also relates to agents which contain the compounds Ia and/or Ib as well as herbicides of type IX or X, it being immaterial whether the herbicidal ingredient and the antidote compound are formulated and applied together or separately or, in the case of separate application, in which sequence the herbicidal ingredient and antidote are applied.

The compounds of the formulae Ia and Ib according to the invention can be obtained in a variety of ways.

Thus, for example, compounds of the formula Ia are obtained by subjecting a carbonyl compound II successively, under conditions similar to those described in J. Org. Chem. 28 (1963), 3041, without isolation of the intermediates, first to nitrosation with a nitrite III in an aqueous acid to give IV, then reduction to the amino keto ester V and conversion thereof directly with a cyanate VI into the arylimidazole VII which is subsequently reacted in the presence or absence of an inert organic solvent and of a base with a halogenating agent conventional in organic chemistry to give Ia. The individual stages in this synthesis are shown below.

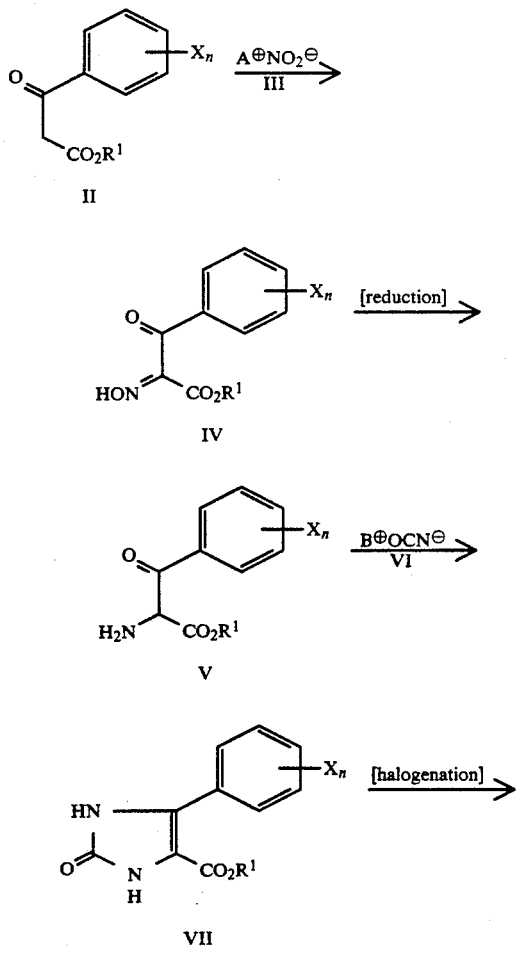

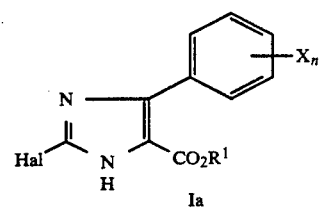

$A^\oplus$ in formula III is an alkali metal ion, e.g. a lithium, sodium or potassium ion.

The nitrosation can be carried out under conventional conditions with a nitrite III in an aqueous acid at from $-10°$ to $60°$ C., preferably $30°$ to $40°$ C., continuously or discontinuously, under atmospheric or superatmospheric pressure (1 to 10 bar).

Examples of suitable acids are carboxylic acids such as formic acid, acetic acid or propionic acid or mineral acids such as hydrochloric acid or sulfuric acid, preferably acetic acid or sulfuric acid.

The isonitroso compound IV can be converted without isolation into the amine V.

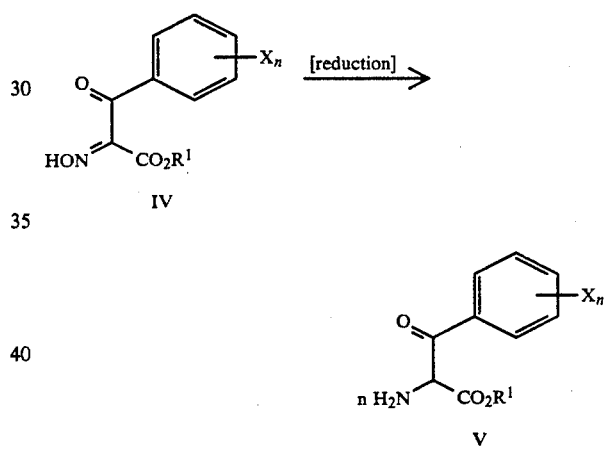

Examples of reducing agents which are used are inorganic salts such as sodium dithionite, sodium bisulfite, sodium sulfite or tin(II) chloride in aqueous acids. Sodium dithionite in the abovementioned aqueous acids is preferred.

However, it is also possible to extract the compounds IV from the reaction mixture using an inert organic solvent which is immiscible with water, and to reduce the isolated product in a catalytic hydrogenation on a noble metal catalyst such as platinum or palladium or nickel-containing catalyst such as Raney nickel in an inert solvent such as acetic acid, methanol, ethanol or tetrahydrofuran at from $25°$ to $50°$ C., preferably $25°$ C., under a pressure of from 1 to 100 bar, preferably 1 to 50 bar, continuously or discontinuously.

The amine V can, without further purification, be cyclized at from $25°$ to $100°$ C. with a cyanate VI where $B^\oplus$ is, for example, an ammonium, sodium or potassium ion, in the abovementioned aqueous acids with or without the addition of an inert organic solvent such as methanol, ethanol or tetrahydrofuran, to give the compound VII.

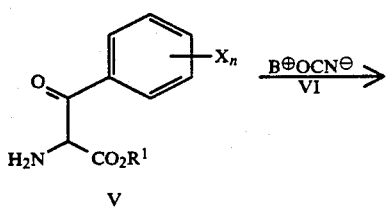

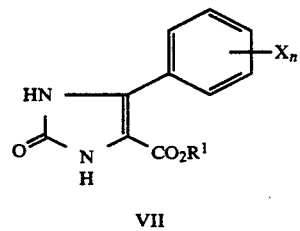

The subsequent reaction of the imidazole VII with a halogenating agent yields Ia.

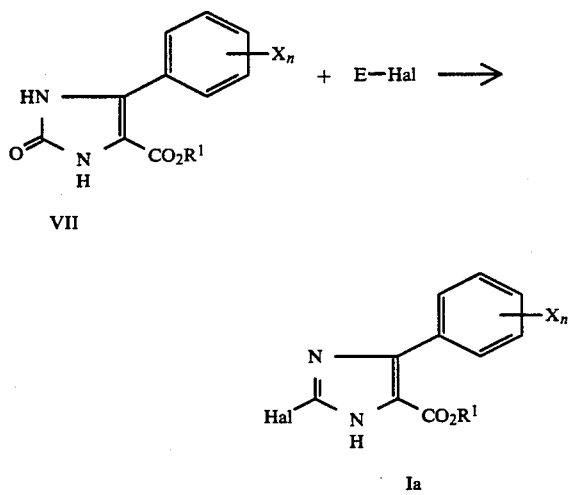

Examples of suitable halogenating agents (E-Hal) are oxyhalides such as phosphorus oxytrichloride or tribromide, thionyl chloride or bromide, or phosgene or halides such as phosphorus pentachloride or pentabromide, phosphorus trichloride or tribromide or sulfur tetrachloride or tetrabromide.

Phosphorus oxychloride or oxybromide is preferred.

The reaction can be carried out with or without solvent at from 0° to 180° C., preferably 40° to 140° C., under atmospheric or superatmospheric pressure (1 to 10 bar, preferably 1 to 3 bar), continuously or discontinuously, with or without the presence of a base.

Bases suitable for this reaction are tertiary amines such as triethylamine, diisopropylamine, N,N-dimethylaniline, N,N-dimethyl-p-aminopyridine, pyridine, isoquinoline, N-methylpyrrolidine, N,N,N',N'-tetramethylethylenediamine, 1,5-diazabicyclo[4.3.0]non-5-ene or 1,8-diazabicyclo[5.4.0]undec-7-ene.

Examples of suitable solvents are halogenated hydrocarbons such as methylene chloride, chloroform, carbon tetrachloride, 1,1,1-trichloroethane or chlorobenzene;

ethers such as diethyl ether, methyl-tert-butyl ether, ethylene glycol dimethyl ether, tetrahydrofuran or dioxane;

nitrated hydrocarbons such as nitrobenzene;

nitriles such as acetonitrile or benzonitrile; or hydrocarbons such hexane, heptane, cyclohexane, decalin, petroleum ether or toluene.

The reaction is preferably carried out without solvent or in chlorobenzene or toluene without a base or with triethylamine or pyridine as base.

The compounds Ib can be obtained, for example, from the 4-aryl-2-haloimidazole-5-carboxylic esters Ia in a conventional manner (Houben-Weyl, vol. E5, pp. 998 et seq.) by alkylation, alkenylation or alkynylation.

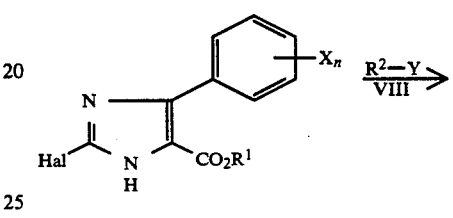

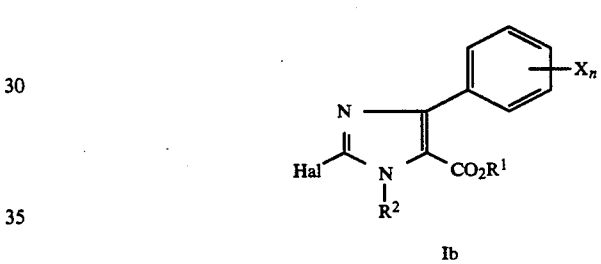

Y in formula VIII is, for example, an easily eliminated group such as halogen, eg. chloride, bromide or iodide; sulfonate, e.g. tosylate, mesylate or triflate, or alkyl sulfate, e.g. methyl sulfate or ethyl sulfate.

The reaction of Ia with VIII is carried out in a solvent in the presence of a base, under atmospheric or superatmospheric pressure (1 to 10 bar), continuously or discontinuously, at from −25° to 200° C., preferably −10° to 150° C.

Examples of suitable bases in this context are alkali metal compounds such as sodium hydride, potassium hydride, sodium methylate, sodium ethylate, potassium tert-butylate, lithium amide, sodium or potassium hydroxide, sodium carbonate, sodium bicarbonate or potassium carbonate or tertiary amines such as triethylamine, N,N-dimethyl-p-aminopyridine, pyridine, N-methylpyrrolidine, quinoline, N,N,N',N'-tetramethylethylenediamine, 1,5-diazabicyclo[4.3.0]non-5-ene or 1,8-diazabicyclo[5.4.0]-undec-7-ene.

Sodium hydride, sodium methylate, potassium tert-butylate or 1,8-diazabicyclo[5.4.0]undec-7-ene is preferred.

Examples of suitable solvents are hydrocarbons such as hexane, heptane, cyclohexane, petroleum ether, decalin, toluene or xylene; ethers such as diethyl ether, methyl tert-butyl ether, ethylene glycol dimethyl ether, tetrahydrofuran or dioxane; amides such as dimethylformamide; sulfoxides such as dimethyl sulfoxide; ketones such as acetone or methyl ethyl ketone or alcohols such as methanol, ethanol or i-propanol.

Tetrahydrofuran, dimethylformamide, toluene or dimethyl sulfoxide is preferred.

Suitable substituents with a view to the specified use of the compounds Ia and/or Ib as crop-protection agents are the following:

$R^1$ alkyls such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 2,2-dimethylpropyl, 1,2-dimethylpropyl, 1-ethylpropyl, hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, or 2-ethylbutyl or 1-propylpropyl, but particularly methyl, ethyl, propyl or 1-methylethyl, alkenyls such as 2-propenyl, 2-butenyl, 3-butenyl, 1-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 2-hexenyl, 3-hexenyl, 4-hexenyl, 5-hexenyl or 1-methyl-2-hexenyl, but especially 2-propenyl, or alkynyls such as 2-propynyl, 2-butynyl, 3-butynyl, 1-methyl-2-propynyl, 2-pentynyl, 3-pentynyl, 4 pentynyl or 2-hexynyl but especially 2-propynylyl;

$R^2$ alkyls such as those mentioned for $R^1$, but especially methyl, ethyl or 1-methylethyl; alkenyls such as those mentioned for $R^1$, but especially 2-propenyl, or alkynyls such as those mentioned for $R^1$, especially 2-propynyl;

X cyano or nitro, alkyls such as methyl, ethyl, propyl, 1-methylethyl, butyl, 1-methylpropyl, 2-methylpropyl or 1,1-dimethylethyl, especially methyl, 1-methylpropyl and 1,1-dimethylethyl; haloalkyls such as trifluoromethyl, difluoromethyl, fluoromethyl, trichloromethyl, dichloromethyl, chloromethyl, 2,2,2-trifluoromethyl, 2,2-difluoroethyl, 2-fluoroethyl, 2,2,2-trichloroethyl, 2-chloroethyl or 2-bromoethyl, especially trifluoromethyl, difluoromethyl or 2,2,2-trifluoroethyl; alkoxy groups such as methoxy, ethoxy, propoxy, 1-methylethoxy, butoxy, 1-methylbutoxy, 2-methylbutoxy or 1,1-dimethylethoxy, especially methoxy, ethoxy or 2-propoxy; haloalkoxy groups such as trifluoromethoxy, trichloromethoxy, fluoromethoxy, 2,2,2-trifluoroethoxy, 1,2,2-trifluoroethoxy or 1,1,2,2-tetrafluoroethoxy, especially trifluoromethoxy or 2,2,2-trifluoroethoxy; alkylthio groups such as methylthio, ethylthio, propylthio, 2-propylthio, butylthio, 1-methylpropylthio, 2-methylpropylthio or 1,1-dimethylethylthio, especially methylthio or ethylthio, alkylsulfinyls such as methylsulfinyl or ethylsulfinyl, alkylsulfonyls such as methylsulfonyl or ethylsulfonyl, haloalkylthio groups such as trifluoromethylthio or trichloromethylthio, carbalkoxy groups such as carbomethoxy or carboethoxy, N,N-dialkylcarbamoyls such as N,N-dimethylcarbamoyl or N,N-diethylcarbamoyl or halogens such as fluorine, chlorine, bromine or iodine, especially fluorine, chlorine or bromine n 0, 1, 2 or 3, especially 0, 1 or 2.

Specific examples of herbicidal (heteroaryloxy) or aryloxy-phenoxyacetic acid derivatives of the formula IX whose tolerability by crop plants can be improved by haloimidazolecarboxylic esters of the formulae Ia and Ib are listed in Table A which follows:

TABLE A $$R^a-O-\phantom{x}\phantom{x}-O-CH(R^c)-CO_2R^b \quad\quad IX$$

| No. | $R^a$ | $R^b$ | $R^c$ | Lit |
|---|---|---|---|---|
| IX.1 | 2,4-dichlorophenyl | CH$_3$ | CH$_3$ | DE-A 22 23 894 |
| IX.2 | 5-trifluoromethylpyridin-2-yl | n-C$_4$H$_9$ | CH$_3$ | BE-A 868 875 |
| IX.3 | 2-acetamido-4-chlorophenyl | C$_2$H$_5$ | CH$_3$ | BE-A 858 618 |
| IX.4 | 3-chloro-5-trifluoromethylpyridin-2-yl | CH$_3$ | CH$_3$ | BE-A 868 875 |
| IX.5 | 6-chloroquinoxalin-2-yl | C$_2$H$_5$ | CH$_3$ | DE-A 30 04 770 |

Specific examples of cyclohexenones of the formula X whose tolerability by crop plants can be improved by haloimidazolecarboxylic esters of the formulae Ia and Ib are listed in Table B which follows.

TABLE B

| No. | $R^d$ | $R^e$ | $R^f$ | $R^g$ | $R^h$ | $R^i$ | Literature |
|---|---|---|---|---|---|---|---|
| X.1 | C$_3$H$_7$ | CH$_2$CH=CH$_2$ | CH$_3$ | CH$_3$ | CO$_2$CH$_3$ | Na | DE-A 2 439 104 |
| X.2 | C$_3$H$_7$ | CH$_2$CH$_3$ | CH$_2$CH(CH$_3$)SCH$_2$CH$_3$ | H | H | H | DE-A 2 822 304 |
| X.3 | C$_2$H$_5$ | CH$_2$CH=CHCl | CH$_2$CH(CH$_3$)SCH$_2$CH$_3$ | H | H | H | US-A 4 440 566 |
| X.4 | C$_3$H$_7$ | CH$_2$CH=CHCl | CH$_2$CH(CH$_3$)SCH$_2$CH$_3$ | H | H | H | US-A 4 440 566 |

TABLE B-continued
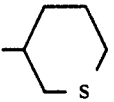
| No. | $R^d$ | $R^e$ | $R^f$ | $R^g$ | $R^h$ | $R^i$ | Literature |
|---|---|---|---|---|---|---|---|
| X.5 | $C_3H_7$ | $C_2CH_5$ | 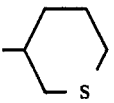 | H | H | H | EP-A 71 707 |
| X.6 | $C_2H_5$ | $C_2H_5$ | 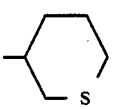 | H | H | H | EP-A 71 707 |
| X.7 | $CH_3$ | $CH_2CH=CHCH_3$ | 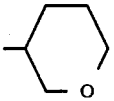 | H | H | H | EP-A 71 707 |
| X.8 | $C_3H_7$ | $C_2H_5$ | 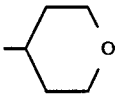 | H | H | H | EP-A 71 707 |
| X.9 | $C_2H_5$ | $CH_2CH=CHCl$ | 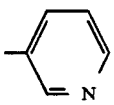 | H | H | H | EP-A 142 741 |
| X.10 | $C_3H_7$ | $C_2H_5$ | 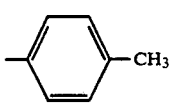 | H | H | H | EP-A 66 195 |
| X.11 | $C_2H_5$ | $C_2H_5$ | 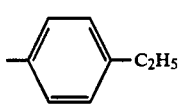 | H | H | H | DE-A 24 39 104 |
| X.12 | $C_2H_5$ | $CH_2CH=CHCH_3$ | 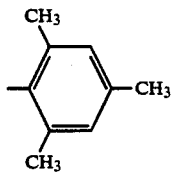 | H | H | H | German application P 38 08 072.9 |
| X.13 | $C_2H_5$ | $C_2H_5$ | 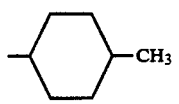 | H | H | H | EP-A 880 301 |
| X.14 | $C_3H_7$ | $CH_2CH=CHCl$ | 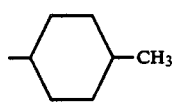 | H | H | H | EP-A 88 299 |
| X.15 | $C_3H_7$ | $CH_2CH=CHCH_3$ | 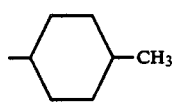 | H | H | H | EP-A 88 299 |

TABLE B-continued

[Structure: cyclohexenone with OR^i, =NOR^e, R^d, R^f, R^g, R^h substituents]

| No. | R^d | R^e | R^f | R^g | R^h | R^i | Literature |
|---|---|---|---|---|---|---|---|
| X.16 | C₂H₅ | CH₂CH=CHCH₃ | 3-isopropyl-5-methyl-isoxazol-yl (CH(CH₃)₂, CH₃ on isoxazole) | H | H | H | EP-A 238 021 |
| X.17 | C₃H₇ | CH₂CH=CHCH₃ | 3-isopropyl-5-methyl-isoxazol-yl (CH(CH₃)₂, CH₃ on isoxazole) | H | H | H | EP-A 238 021 |
| X.18 | C₂H₅ | CH₂CH=CHCl | 4-(propargyloxy)phenyl (—OCH₂—C≡CH) | H | H | H | EP-A 137 174 |
| X.19 | C₃H₇ | C₂H₅ | 4-(ethoxymethyl)phenyl (—CH₂OC₂H₅) | H | H | H | EP-A 2 137 200 |
| X.20 | C₃H₇ | C₂H₅ | 3,4-dibromo-3-methyl-tetrahydropyranyl | H | H | H | EP-A 230 235 |
| X.21 | C₃H₇ | CH₂CH=CHCl | 3,4-dibromo-3-methyl-tetrahydropyranyl | H | H | H | EP-A 230 235 |
| X.22 | C₃H₇ | CH₂CH=CHCl | 2,6,6-trimethylcyclohex-1-enyl (H₃C, CH₃, CH₃, CH₃) | H | H | H | EP-A 46 860 |
| X.23 | C₃H₇ | C₂H₅ | cyclohexyl | H | H | H | JP-A 540 191 945 |
| X.24 | C₃H₇ | C₂H₅ | cyclohex-1-enyl | H | H | H | EP-A 46 860 |
| X.25 | CH₃ | CH₂CH=CHCl | 4-methylcyclohexyl (—CH₃) | H | H | H | EP-A 88 299 |
| X.26 | C₃H₇ | C₂H₅ | 4-(trifluoromethyl)phenyl (—CF₃) | H | H | K | EP-A 137 174 |

TABLE B-continued

| No. | $R^d$ | $R^e$ | $R^f$ | $R^g$ | $R^h$ | $R^i$ | Literature |
|---|---|---|---|---|---|---|---|
| X.27 | $C_2H_5$ | $CH_2CH=CHCl$ | (2,6,6-trimethylcyclohex-1-enyl with H$_3$C, H$_3$C, CH$_3$ substituents) | | H | H | H | EP-A 46 860 |

The herbicidal active ingredients and antidotes may be applied together or separately to the leaves and shoots of the crop plants and unwanted plants. Preferably, the antidote is applied together with the herbicidal active ingredient. If the components are applied separately, the antidote is applied first to the field and then the herbicidal active ingredient. The herbicidal active ingredient and antidote may be formulated together or separately as spray agents in the form of suspensions, emulsions or solutions.

Treatment of the crop plant seed with the antidote prior to sowing is also feasible. The herbicidal active ingredient is then applied to the field on its own in conventional manner.

For herbicidal (heteroaryloxy)-phenoxyacetic or -propionic acid derivatives of the formula IX, the amount of antidotally active compound varies, depending on the crop. The ratios may vary over a wide range, and are also dependent on the structure of the (heteroaryloxy)phenoxyacetic or -propionic acid derivatives IX and on the crop involved. Suitable ratios of herbicidal active ingredient to antidote are from 1:4 to 1:0.01, and preferably from 1:4 to 1:0.1, parts by weight.

For the same cyclohexenone derivative X, the amount of antidote varies, depending on the crop. The ratios in which a cyclohexenone derivative and a haloimidazolecarboxylic ester of the formula Ia and/or Ib are used may vary over a wide range, and are dependent on the structure of the cyclohexenone derivative, the haloimidazolecarboxylic ester of the formula Ia and/or Ib, and the crop involved. Suitable ratios of herbicidal active ingredient to safener are from 1:4 to 1:0.01, and preferably from 1:4 to 1:0.25, parts by weight.

The novel herbicidal agents may contain, in addition to the haloimidazolecarboxylic ester of the formula Ia and/or Ib as safener and the herbicide from the group of the (heteroaryloxy)phenoxyacetic or -propionic acids IX or cyclohexenones X, other herbicidal or growth-regulating active ingredients having a different chemical structure without the safening effect being impaired.

The agents according to the invention, or—when applied separately—the herbicidal active ingredients and the safener, are applied for instance in the form of directly sprayable solutions, powders, suspensions (including high-percentage aqueous, oily or others), dispersions, emulsions, oil dispersions, pastes, dusts, broadcasting agents or granules by spraying, atomizing, dusting, broadcasting or pouring. The forms of application depend entirely on the purpose for which the active ingredients are to be used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote as such or dissolved in an oil or solvent may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

SYNTHESIS EXAMPLES

The directions given in the examples which follow were used with appropriately modified starting compounds to obtain further compounds of the formulas Ia and Ib. The compounds obtained are given with their physical data in the tables below; compounds without these data may be prepared analogously from the appropriate materials. In view of their close structural relationship to the compounds which have been prepared and investigated, they are expected to have a similar action.

EXAMPLE 1 a) Ethyl 4-phenyl-2-imidazolone-5-carboxylate

At 35° to 45° C., a solution of 35 g of sodium nitrite in 100 ml of water was added to 112 g (0.582 mol) of ethyl benzoylacetate in 130 ml of acetic acid. The mixture was stirred for 30 minutes at this temperature, and then 500 ml of water was added.

After the mixture had been stirred for one hour, 302 g of sodium dithionite in 600 ml of water was added, the resulting mixture was stirred for 30 minutes and then 157 g of potassium cyanate was introduced. The solution was heated briefly to 70° to 80° C., and then left to stand overnight at room temperature. Extraction with ethyl acetate gave ethyl 4-phenyl-2-imidazolone-5-carboxylate of m.p. 109° to 112° C.

b) Ethyl 2-chloro-4-phenylimidazole-5-carboxylate 20 g (0.086 mol) of ethyl 4-phenyl-2-imidazolone-5-carboxylate was refluxed for 5 hours with 250 ml of phosphorus oxychloride. The excess phosphorus oxychloride was removed under reduced pressure, the residue was poured onto ice, the pH was adjusted to 5–6 with ammonia, and the crude product was extracted with ethyl acetate, dried and evaporated down. Chromatography of the residue on silica gel (developer: ethyl acetate/pentane) gave ethyl 2-chloro-4-phenylimidazole-5-carboxylate (compound no. 1.001) of m.p. 128° to 129° C.

EXAMPLE 2

Ethyl 2-chloro-1-methyl-4-phenylimidazole-5-carboxylate 0.6 g of sodium hydride was added to a solution of 7 g (0.028 mol) of ethyl 2-chloro-4-phenylimidazole-5-carboxylate in 25 ml of dimethylformamide. Upon completion of gas evolution, 4.2 g (0.033 mol) of dimethyl sulfate was added and the mixture was heated at 80° C. for 1½ hours. The dimethylformamide was removed under reduced pressure and the residue was poured into dilute ammonium hydroxide. After extraction with ethyl acetate, drying and removal of the solvent, chromatography on silica gel (developer: ethyl acetate/pentane) gave ethyl 2-chloro-1-methyl-4-phenylimidazole-5-carboxylate (compound no. 2.001) of m.p. 54° to 55° C.

TABLE 1

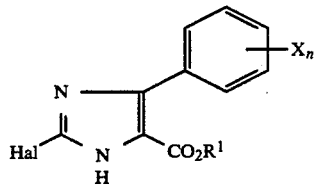

| Comp. no. | Hal | $X_n$ | $R^1$ | mp [°C.] |
|---|---|---|---|---|
| 1.001 | Cl | H | $CH_2CH_3$ | 128–129 |
| 1.002 | Cl | H | $CH_3$ | |
| 1.003 | Cl | H | $CH_2CH_2CH_3$ | |
| 1.004 | Cl | H | $CH(CH_3)_2$ | |
| 1.005 | Cl | 2-F | $CH_3$ | |
| 1.006 | Cl | 2-F | $CH_2CH_3$ | 130–132 |
| 1.007 | Cl | 3-F | $CH_3$ | |
| 1.008 | Cl | 3-F | $CH_2CH_3$ | |
| 1.009 | Cl | 4-F | $CH_3$ | |
| 1.010 | Cl | 4-F | $CH_2CH_3$ | 77–80 |
| 1.011 | Cl | 2-Cl | $CH_3$ | |
| 1.012 | Cl | 2-Cl | $CH_2CH_3$ | |
| 1.013 | Cl | 3-Cl | $CH_3$ | |
| 1.014 | Cl | 3-Cl | $CH_2CH_3$ | |
| 1.015 | Cl | 4-Cl | $CH_3$ | |
| 1.016 | Cl | 4-Cl | $CH_2CH_3$ | |
| 1.017 | Cl | 2-Br | $CH_3$ | |
| 1.018 | Cl | 2-Br | $CH_2CH_3$ | |
| 1.019 | Cl | 3-Br | $CH_3$ | |
| 1.020 | Cl | 3-Br | $CH_2CH_3$ | |
| 1.021 | Cl | 4-Br | $CH_3$ | |
| 1.022 | Cl | 4-Br | $CH_2CH_3$ | |
| 1.023 | Cl | 2-F, 4-F | $CH_3$ | |
| 1.024 | Cl | 2-F, 4-F | $CH_2CH_3$ | |
| 1.025 | Cl | 2-F, 4-F | $CH_2CH_2CH_3$ | |

TABLE 1-continued

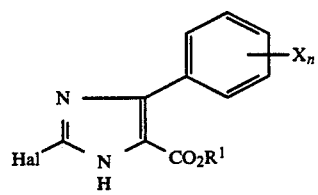

| Comp. no. | Hal | $X_n$ | $R^1$ | mp [°C.] |
|---|---|---|---|---|
| 1.026 | Cl | 2-F, 4-F | $CH_2CH=CH_2$ | |
| 1.027 | Cl | 2-F, 4-F | $CH_2C\equiv CH$ | |
| 1.028 | Cl | 3-F, 4-F | $CH_3$ | |
| 1.029 | Cl | 3-F, 4-F | $CH_2CH_3$ | |
| 1.030 | Cl | 2-F, 3-F | $CH_3$ | |
| 1.031 | Cl | 2-F, 3-F | $CH_2CH_3$ | |
| 1.032 | Cl | 2-F, 5-F | $CH_3$ | |
| 1.033 | Cl | 2-F, 5-F | $CH_2CH_3$ | |
| 1.034 | Cl | 2-F, 6-F | $CH_3$ | |
| 1.035 | Cl | 2-F, 6-F | $CH_2CH_3$ | |
| 1.036 | Cl | 2-Cl, 3-Cl | $CH_3$ | |
| 1.037 | Cl | 2-Cl, 3-Cl | $CH_2CH_3$ | |
| 1.038 | Cl | 2-Cl, 4-Cl | $CH_3$ | |
| 1.039 | Cl | 2-Cl, 4-Cl | $CH_2CH_3$ | |
| 1.040 | Cl | 2-Cl, 4-Cl | $CH_2CH_2CH_3$ | |
| 1.041 | Cl | 2-Cl, 4-Cl | $CH(CH_3)_2$ | |
| 1.042 | Cl | 2-Cl, 4-Cl | $CH_2CH=CH_2$ | |
| 1.043 | Cl | 2-Cl, 4-Cl | $CH_2C\equiv CH$ | |
| 1.044 | Cl | 2-Cl, 5-Cl | $CH_3$ | |
| 1.045 | Cl | 2-Cl, 5-Cl | $CH_2CH_3$ | |
| 1.046 | Cl | 2-Cl, 6-Cl | $CH_3$ | |
| 1.047 | Cl | 2-Cl, 6-Cl | $CH_2CH_3$ | |
| 1.048 | Cl | 3-Cl, 4-Cl | $CH_3$ | |
| 1.049 | Cl | 3-Cl, 4-Cl | $CH_2CH_3$ | |
| 1.050 | Cl | 3-Cl, 5-Cl | $CH_3$ | |
| 1.051 | Cl | 3-Cl, 5-Cl | $CH_2CH_3$ | |
| 1.052 | Cl | 2-Cl, 4-Cl, 6-Cl | $CH_3$ | |
| 1.053 | Cl | 2-Cl, 4-Cl, 6-Cl | $CH_2CH_3$ | |
| 1.054 | Cl | 2-Br, 4-Br | $CH_3$ | |
| 1.055 | Cl | 2-Br, 4-Br | $CH_2CH_3$ | |
| 1.056 | Cl | 2-F, 4-Cl | $CH_3$ | |
| 1.057 | Cl | 2-F, 4-Cl | $CH_2CH_3$ | |
| 1.058 | Cl | 2-$NO_2$ | $CH_3$ | |
| 1.059 | Cl | 2-$NO_2$ | $CH_2CH_3$ | |
| 1.060 | Cl | 3-$NO_2$ | $CH_3$ | |
| 1.061 | Cl | 3-$NO_2$ | $CH_2CH_3$ | |
| 1.062 | Cl | 4-$NO_2$ | $CH_3$ | |
| 1.063 | Cl | 4-$NO_2$ | $CH_2CH_3$ | |
| 1.064 | Cl | 2-$NO_2$, 4-$NO_2$ | $CH_3$ | |
| 1.065 | Cl | 2-$NO_2$, 4-$NO_2$ | $CH_2CH_3$ | |
| 1.066 | Cl | 2-Cl, 4-$NO_2$ | $CH_3$ | |
| 1.067 | Cl | 2-Cl, 4-$NO_2$ | $CH_2CH_3$ | |
| 1.068 | Cl | 2-$NO_2$, 4-Cl | $CH_3$ | |
| 1.069 | Cl | 2-$NO_2$, 4-Cl | $CH_2CH_3$ | |
| 1.070 | Cl | 2-CN | $CH_3$ | |
| 1.071 | Cl | 2-CN | $CH_2CH_3$ | |
| 1.072 | Cl | 4-CN | $CH_3$ | |
| 1.073 | Cl | 4-CN | $CH_2CH_3$ | 172–173 |
| 1.074 | Cl | 2-Cl, 4-CN | $CH_3$ | |
| 1.075 | Cl | 2-Cl, 4-CN | $CH_2CH_3$ | |
| 1.076 | Cl | 2-F, 4-CN | $CH_3$ | |
| 1.077 | Cl | 2-F, 4-CN | $CH_2CH_3$ | |
| 1.078 | Cl | 2-$CH_3$ | $CH_3$ | |
| 1.079 | Cl | 2-$CH_3$ | $CH_2CH_3$ | |
| 1.080 | Cl | 3-$CH_3$ | $CH_3$ | |
| 1.081 | Cl | 3-$CH_3$ | $CH_2CH_3$ | |
| 1.082 | Cl | 4-$CH_3$ | $CH_3$ | |
| 1.083 | Cl | 4-$CH_3$ | $CH_2CH_3$ | 150–151 |
| 1.084 | Cl | 4-$C(CH_3)_3$ | $CH_3$ | |
| 1.085 | Cl | 4-$C(CH_3)_3$ | $CH_2CH_3$ | |
| 1.086 | Cl | 2-$CH_3$, 4-$CH_3$ | $CH_3$ | |
| 1.087 | Cl | 2-$CH_3$, 4-$CH_3$ | $CH_2CH_3$ | |
| 1.088 | Cl | 2-$CH_3$, 6-$CH_3$ | $CH_3$ | |
| 1.089 | Cl | 2-$CH_3$, 6-$CH_3$ | $CH_2CH_3$ | |
| 1.090 | Cl | 2-$CH_3$, 4-$CH_3$, 6-$CH_3$ | $CH_3$ | |
| 1.091 | Cl | 2-$CH_3$-4-$CH_3$, 6-$CH_3$ | $CH_2CH_3$ | |
| 1.092 | Cl | 2-$CF_3$ | $CH_3$ | |
| 1.093 | Cl | 2-$CF_3$ | $CH_2CH_3$ | |
| 1.094 | Cl | 3-$CF_3$ | $CH_3$ | |
| 1.095 | Cl | 3-$CF_3$ | $CH_2CH_3$ | |

TABLE 1-continued

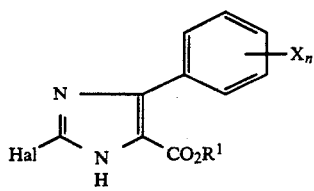

| Comp. no. | Hal | $X_n$ | $R^1$ | mp [°C.] |
|---|---|---|---|---|
| 1.096 | Cl | 4-$CF_3$ | $CH_3$ | |
| 1.097 | Cl | 4-$CF_3$ | $CH_2CH_3$ | |
| 1.098 | Cl | 2-Cl, 4-$CF_3$ | $CH_3$ | |
| 1.099 | Cl | 2-Cl, 4-$CF_3$ | $CH_2CH_3$ | |
| 1.100 | Cl | 2-F, 4-$CF_3$ | $CH_3$ | |
| 1.101 | Cl | 2-F, 4-$CF_3$ | $CH_2CH_3$ | |
| 1.102 | Cl | 4-$CF_2Cl$ | $CH_3$ | |
| 1.103 | Cl | 4-$CF_2Cl$ | $CH_2CH_3$ | |
| 1.104 | Cl | 4-$OCF_2CHF_2$ | $CH_3$ | |
| 1.105 | Cl | 4-$OCF_2CHCF_2$ | $CH_2CH_3$ | |
| 1.106 | Cl | 4-$OCF_3$ | $CH_3$ | |
| 1.107 | Cl | 4-$OCF_3$ | $CH_2CH_3$ | |
| 1.108 | Cl | 2-$OCH_3$ | $CH_3$ | |
| 1.109 | Cl | 2-$OCH_3$ | $CH_2CH_3$ | |
| 1.110 | Cl | 3-$OCH_3$ | $CH_3$ | |
| 1.111 | Cl | 3-$OCH_3$ | $CH_2CH_3$ | |
| 1.112 | Cl | 4-$OCH_3$ | $CH_3$ | |
| 1.113 | Cl | 4-$OCH_3$ | $CH_2CH_3$ | |
| 1.114 | Cl | 2-$OCH_3$, 4-$OCH_3$ | $CH_3$ | |
| 1.115 | Cl | 2-$OCH_3$, 4-$OCH_3$ | $CH_2CH_3$ | |
| 1.116 | Cl | 2-$OCH_3$, 6-$OCH_3$ | $CH_3$ | |
| 1.117 | Cl | 2-$OCH_3$, 6-$OCH_3$ | $CH_2CH_3$ | |
| 1.118 | Cl | 4-$OCH_2CH_3$ | $CH_3$ | |
| 1.119 | Cl | 4-$OCH_2CH_3$ | $CH_2CH_3$ | |
| 1.120 | Cl | 2-$SCH_3$ | $CH_3$ | |
| 1.121 | Cl | 2-$SCH_3$ | $CH_2CH_3$ | |
| 1.122 | Cl | 4-$SCH_3$ | $CH_3$ | |
| 1.123 | Cl | 4-$SCH_3$ | $CH_2CH_3$ | |
| 1.124 | Cl | 2-$SOCH_3$ | $CH_3$ | |
| 1.125 | Cl | 2-$SOCH_3$ | $CH_2CH_3$ | |
| 1.126 | Cl | 2-$SO_2CH_3$ | $CH_3$ | |
| 1.127 | Cl | 2-$SO_2CH_3$ | $CH_2CH_3$ | |
| 1.128 | Cl | 2-$CO_2CH_3$ | $CH_3$ | |
| 1.129 | Cl | 2-$CO_2CH_3$ | $CH_2CH_3$ | |
| 1.130 | Cl | 2-$CON(CH_3)_2$ | $CH_3$ | |
| 1.131 | Cl | 2-$CON(CH_3)_2$ | $CH_2CH_3$ | |
| 1.132 | Br | H | $CH_3$ | |
| 1.133 | Br | H | $CH_2CH_3$ | |
| 1.134 | Br | 4-F | $CH_3$ | |
| 1.135 | Br | 4-Cl | $CH_2CH_3$ | |
| 1.136 | Br | 4-Cl | $CH_3$ | |
| 1.137 | Br | 4-Br | $CH_2CH_3$ | |
| 1.138 | Br | 2-Cl, 4-Cl | $CH_3$ | |
| 1.139 | Br | 2-Cl, 4-Cl | $CH_2CH_3$ | |
| 1.140 | Br | 2-Cl, 6-Cl | $CH_3$ | |
| 1.141 | Br | 2-Cl, 6-Cl | $CH_2CH_3$ | |
| 1.142 | Br | 2-F, 4-F | $CH_3$ | |
| 1.143 | Br | 2-F, 4-F | $CH_2CH_3$ | |
| 1.144 | Br | 2-F, 6-F | $CH_2CH_3$ | |
| 1.145 | Br | 2-Cl, 4-Cl, 6-Cl | $CH_2CH_3$ | |
| 1.146 | Br | 4-$NO_2$ | $CH_2CH_3$ | |
| 1.147 | Br | 2-$NO_2$, 4-$NO_2$ | $CH_2CH_3$ | |
| 1.148 | Br | 2-Cl, 4-$NO_2$ | $CH_2CH_3$ | |
| 1.149 | Br | 2-$NO_2$, 4-Cl | $CH_2CH_3$ | |
| 1.150 | Br | 2-$CH_3$, 4-$CH_3$ | $CH_2CH_3$ | |
| 1.151 | Br | 2-$CH_3$, 6-$CH_3$ | $CH_2CH_3$ | |
| 1.152 | Br | 4-$CF_3$ | $CH_2CH_3$ | |
| 1.153 | Br | 3-$CF_3$ | $CH_2CH_3$ | |
| 1.154 | Br | 2-F, 4-$CF_3$ | $CH_2CH_3$ | |
| 1.155 | Br | 2-$OCH_3$, 4-$OCH_3$ | $CH_2CH_3$ | |
| 1.156 | Br | 2-$OCH_3$, 6-$OCH_3$ | $CH_2CH_3$ | |
| 1.157 | Br | 4-$SCF_3$ | $CH_2CH_3$ | |

TABLE 2

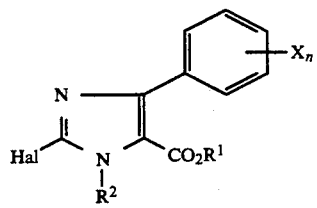

| Comp. no. | Hal | $X_n$ | $R^1$ | $R^2$ | mp [°C.] |
|---|---|---|---|---|---|
| 2.001 | Cl | H | $CH_2CH_3$ | $CH_3$ | 54–55 |
| 2.002 | Cl | H | $CH_2CH_3$ | $CH_2CH_3$ | |
| 2.003 | Cl | H | $CH_2CH_3$ | $CH_2CH_2CH_3$ | |
| 2.004 | Cl | H | $CH_2CH_3$ | $CH(CH_3)_2$ | |
| 2.005 | Cl | H | $CH_3$ | $CH_3$ | |
| 2.006 | Cl | H | $CH_3$ | $CH(CH_3)_2$ | |
| 2.007 | Cl | 2-F | $CH_2CH_3$ | $CH_3$ | |
| 2.008 | Cl | 2-F | $CH_2CH_3$ | $CH_2CH=CH_2$ | |
| 2.009 | Cl | 3-F | $CH_2CH_3$ | $CH_3$ | |
| 2.010 | Cl | 4-F | $CH_2CH_3$ | $CH_3$ | oil [$^1$H-NMR($d_6$-DMSO): 3.83(s, 3H); 4.08–4.15(q, 2H)] |
| 2.011 | Cl | 4-F | $CH_2CH_3$ | $CH_2CH_3$ | |
| 2.012 | Cl | 4-F | $CH_3$ | $CH_3$ | |
| 2.013 | Cl | 2-Cl | $CH_3$ | $CH_3$ | |
| 2.014 | Cl | 2-Cl | $CH_2CH_3$ | $CH_3$ | |
| 2.015 | Cl | 4-Cl | $CH_3$ | $CH_3$ | |
| 2.016 | Cl | 4-Cl | $CH_2CH_3$ | $CH_3$ | |
| 2.017 | Cl | 4-Br | $CH_3$ | $CH_3$ | |
| 2.018 | Cl | 4-Br | $CH_2CH_3$ | $CH_3$ | |
| 2.019 | Cl | 2-F, 4-F | $CH_3$ | $CH_3$ | |
| 2.020 | Cl | 2-F, 4-F | $CH_3$ | $CH_2C\equiv CH$ | |
| 2.021 | Cl | 2-F, 4-F | $CH_3$ | $CH(CH_3)_2$ | |
| 2.022 | Cl | 2-F, 4-F | $CH_2CH_3$ | $CH_3$ | |
| 2.023 | Cl | 2-F, 4-F | $CH_2CH_3$ | $CH_2CH_3$ | |
| 2.024 | Cl | 2-F, 4-F | $CH_2CH_3$ | $CH(CH_3)_2$ | |
| 2.025 | Cl | 3-F, 4-F | $CH_2CH_3$ | $CH_3$ | |
| 2.026 | Cl | 2-F, 3-F | $CH_2CH_3$ | $CH_3$ | |
| 2.027 | Cl | 2-F, 5-F | $CH_2CH_3$ | $CH_3$ | |
| 2.028 | Cl | 2-F, 6-F | $CH_3$ | $CH_3$ | |
| 2.029 | Cl | 2-F, 6-F | $CH_2CH_3$ | $CH_3$ | |
| 2.030 | Cl | 2-F, 6-F | $CH_2CH_3$ | $CH_2CH_3$ | |
| 2.031 | Cl | 2-F, 6-F | $CH_2CH_3$ | $CH(CH_3)_2$ | |
| 2.032 | Cl | 2-Cl, 3-Cl | $CH_3$ | $CH_3$ | |
| 2.033 | Cl | 2-Cl, 3-Cl | $CH_2CH_3$ | $CH_3$ | |
| 2.034 | Cl | 2-Cl, 4-Cl | $CH_3$ | $CH_3$ | |
| 2.035 | Cl | 2-Cl, 4-Cl | $CH_3$ | $CH_2CH_3$ | |
| 2.036 | Cl | 2-Cl, 4-Cl | $CH_3$ | $CH(CH_3)_2$ | |
| 2.037 | Cl | 2-Cl, 4-Cl | $CH_2CH_3$ | $CH_3$ | |
| 2.038 | Cl | 2-Cl, 4-Cl | $CH_2CH_3$ | $CH_2CH_3$ | |
| 2.039 | Cl | 2-Cl, 4-Cl | $CH_2CH_3$ | $CH(CH_3)_2$ | |
| 2.040 | Cl | 2-Cl, 4-Cl | $CH_2CH=CH_2$ | $CH_3$ | |
| 2.041 | Cl | 2-Cl, 4-Cl | $CH_2CH=CH_2$ | $CH_2CH_3$ | |
| 2.042 | Cl | 2-Cl, 4-Cl | $CH_2CH=CH_2$ | $CH(CH_3)_2$ | |
| 2.043 | Cl | 2-Cl, 4-Cl | $CH_2C\equiv CH$ | $CH_3$ | |
| 2.044 | Cl | 2-Cl, 4-Cl | $CH_2C\equiv CH$ | $CH_2CH_3$ | |
| 2.045 | Cl | 2-Cl, 4-Cl | $CH_2C\equiv CH$ | $CH(CH_3)_2$ | |
| 2.046 | Cl | 2-Cl, 5-Cl | $CH_3$ | $CH_3$ | |
| 2.047 | Cl | 2-Cl, 5-Cl | $CH_2CH_3$ | $CH_3$ | |
| 2.048 | Cl | 2-Cl, 6-Cl | $CH_3$ | $CH_3$ | |
| 2.049 | Cl | 2-Cl, 6-Cl | $CH_2CH_3$ | $CH_3$ | |
| 2.050 | Cl | 3-Cl, 4-Cl | $CH_3$ | $CH_3$ | |
| 2.051 | Cl | 3-Cl, 4-Cl | $CH_2CH_3$ | $CH_3$ | |
| 2.052 | Cl | 3-Cl, 5-Cl | $CH_2CH_3$ | $CH_3$ | |
| 2.053 | Cl | 2-Cl, 4-Cl, 6-Cl | $CH_3$ | $CH_3$ | |
| 2.054 | Cl | 2-Cl, 4-Cl, 6-Cl | $CH_2CH_3$ | $CH_3$ | |
| 2.055 | Cl | 2-Br, 4-Br | $CH_3$ | $CH_3$ | |
| 2.056 | Cl | 2-Br, 4-Br | $CH_3$ | $CH(CH_3)_2$ | |
| 2.057 | Cl | 2-Br, 4-Br | $CH_2CH_3$ | $CH_3$ | |
| 2.058 | Cl | 2-Br, 4-Br | $CH_2CH_3$ | $CH(CH_3)_2$ | |
| 2.059 | Cl | 2-F, 4-Cl | $CH_3$ | $CH_3$ | |
| 2.060 | Cl | 2-F, 4-Cl | $CH_2CH_3$ | $CH_3$ | |
| 2.061 | Cl | 2-$NO_2$ | $CH_2CH_3$ | $CH_3$ | |
| 2.062 | Cl | 3-$NO_2$ | $CH_2CH_3$ | $CH_3$ | |
| 2.063 | Cl | 4-$NO_2$ | $CH_3$ | $CH_3$ | |
| 2.064 | Cl | 4-$NO_2$ | $CH_2CH_3$ | $CH_3$ | |
| 2.065 | Cl | 2-$NO_2$, 4-$NO_4$ | $CH_3$ | $CH_3$ | |
| 2.066 | Cl | 2-$NO_2$, 4-$NO_4$ | $CH_3$ | $CH_2CH_3$ | |
| 2.067 | Cl | 2-$NO_2$, 4-$NO_4$ | $CH_2CH_3$ | $CH_3$ | |
| 2.068 | Cl | 2-$NO_2$, 4-$NO_4$ | $CH_2CH_3$ | $CH_2CH_3$ | |
| 2.069 | Cl | 2-Cl, 4-$NO_2$ | $CH_3$ | $CH_3$ | |

TABLE 2-continued

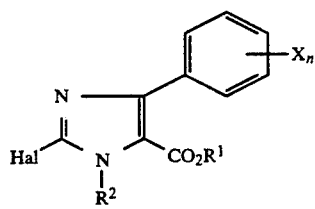

| Comp. no. | Hal | $X_n$ | $R^1$ | $R^2$ | mp [°C.] |
|---|---|---|---|---|---|
| 2.070 | Cl | 2-Cl,4-NO$_2$ | CH$_2$CH$_3$ | CH$_3$ | |
| 2.071 | Cl | 2-NO$_2$, 4-Cl | CH$_3$ | CH$_3$ | |
| 2.072 | Cl | 2-NO$_2$, 4-Cl | CH$_2$CH$_3$ | CH$_3$ | |
| 2.073 | Cl | 2-CN | CH$_2$CH$_3$ | CH$_3$ | |
| 2.074 | Cl | 4-CN | CH$_3$ | CH$_3$ | |
| 2.075 | Cl | 4-CN | CH$_2$CH$_3$ | CH$_3$ | |
| 2.076 | Cl | 2-Cl, 4-CN | CH$_3$ | CH$_3$ | |
| 2.077 | Cl | 2-Cl, 4-CN | CH$_2$CH$_3$ | CH$_3$ | |
| 2.078 | Cl | 2-F, 4-CN | CH$_2$CH$_3$ | CH$_3$ | |
| 2.079 | Cl | 2-CH$_3$ | CH$_2$CH$_3$ | CH$_3$ | |
| 2.080 | Cl | 3-CH$_3$ | CH$_2$CH$_3$ | CH$_3$ | |
| 2.081 | Cl | 4-CH$_3$ | CH$_3$ | CH$_3$ | |
| 2.082 | Cl | 4-CH$_3$ | CH$_2$CH$_3$ | CH$_3$ | 73-75 |
| 2.083 | Cl | 2-CH$_3$, 4-CH$_3$ | CH$_3$ | CH$_3$ | |
| 2.084 | Cl | 2-CH$_3$, 4-CH$_3$ | CH$_2$CH$_3$ | CH$_3$ | |
| 2.085 | Cl | 2-CH$_3$, 6-CH$_3$ | CH$_3$ | CH$_3$ | |
| 2.086 | Cl | 2-CH$_3$, 6-CH$_3$ | CH$_2$CH$_3$ | CH$_3$ | |
| 2.087 | Cl | 2-CH$_3$, 4-CH$_3$, 6-CH$_3$ | CH$_3$ | CH$_3$ | |
| 2.088 | Cl | 2-CH$_3$, 4-CH$_3$, 6-CH$_3$ | CH$_2$CH$_3$ | CH$_3$ | |
| 2.089 | Cl | 2-CF$_3$ | CH$_2$CH$_3$ | CH$_3$ | |
| 2.090 | Cl | 3-CF$_3$ | CH$_3$ | CH$_3$ | |
| 2.091 | Cl | 3-CF$_3$ | CH$_2$CH$_3$ | CH$_3$ | |
| 2.092 | Cl | 4-CF$_3$ | CH$_3$ | CH$_3$ | |
| 2.093 | Cl | 4-CF$_3$ | CH$_2$CH$_3$ | CH$_3$ | |
| 2.094 | Cl | 2-Cl, 4-CF$_3$ | CH$_3$ | CH$_3$ | |
| 2.095 | Cl | 2-Cl, 4-CF$_3$ | CH$_3$ | CH(CH$_3$)$_2$ | |
| 2.096 | Cl | 2-Cl, 4-CF$_3$ | CH$_2$CH$_3$ | CH$_3$ | |
| 2.097 | Cl | 2-Cl, 4-CF$_3$ | CH$_2$CH$_3$ | CH$_2$CH$_3$ | |
| 2.098 | Cl | 4-OCF$_3$ | CH$_2$CH$_3$ | CH$_3$ | |
| 2.099 | Cl | 2-OCH$_3$ | CH$_2$CH$_3$ | CH$_3$ | |
| 2.100 | Cl | 3-OCH$_3$ | CH$_2$CH$_3$ | CH$_3$ | |
| 2.101 | Cl | 4-OCH$_3$ | CH$_3$ | CH$_3$ | |
| 2.102 | Cl | 4-OCH$_3$ | CH$_2$CH$_3$ | CH$_3$ | |
| 2.103 | Cl | 2-OCH$_3$, 4-OCH$_3$ | CH$_3$ | CH$_3$ | |
| 2.104 | Cl | 2-OCH$_3$, 4-OCH$_3$ | CH$_2$CH$_3$ | CH$_3$ | |
| 2.105 | Cl | 2-OCH$_3$, 6-OCH$_3$ | CH$_3$ | CH$_3$ | |
| 2.106 | Cl | 2-OCH$_3$, 6-OCH$_3$ | CH$_2$CH$_3$ | CH$_3$ | |
| 2.107 | Cl | 2-SCH$_3$ | CH$_2$CH$_3$ | CH$_3$ | |
| 2.108 | Cl | 4-SCH$_3$ | CH$_2$CH$_3$ | CH$_3$ | |
| 2.109 | Cl | 2-SOCH$_3$ | CH$_2$CH$_3$ | CH$_3$ | |
| 2.110 | Cl | 2-SO$_2$CH$_3$ | CH$_2$CH$_3$ | CH$_3$ | |
| 2.111 | Cl | 2-CO$_2$CH$_3$ | CH$_2$CH$_3$ | CH$_3$ | |
| 2.112 | Cl | 2-CON(CH$_3$)$_2$ | CH$_2$CH$_3$ | CH$_3$ | |
| 2.113 | Br | H | CH$_2$CH$_3$ | CH$_3$ | |
| 2.114 | Br | 4-F | CH$_2$CH$_3$ | CH$_3$ | |
| 2.115 | Br | 4-Cl | CH$_2$CH$_3$ | CH$_3$ | |
| 2.116 | Br | 4-Br | CH$_2$CH$_3$ | CH$_3$ | |
| 2.117 | Br | 2-Cl, 4-Cl | CH$_3$ | CH$_3$ | |
| 2.118 | Br | 2-Cl, 4-Cl | CH$_2$CH$_3$ | CH$_3$ | |
| 2.119 | Br | 2-Cl, 6-Cl | CH$_2$CH$_3$ | CH$_3$ | |
| 2.120 | Br | 2-F, 4-F | CH$_2$CH$_3$ | CH$_3$ | |
| 2.121 | Br | 2-F, 6-F | CH$_2$CH$_3$ | CH$_3$ | |
| 2.122 | Br | 2-Cl, 4-Cl, 6-Cl | CH$_2$CH$_3$ | CH$_3$ | |
| 2.123 | Br | 4-NO$_2$ | CH$_2$CH$_3$ | CH$_3$ | |
| 2.124 | Br | 2-NO$_2$, 4-NO$_2$ | CH$_2$CH$_3$ | CH$_3$ | |
| 2.125 | Br | 2-Cl, 4-NO$_2$ | CH$_2$CH$_3$ | CH$_3$ | |
| 2.126 | Br | 2-NO$_2$, 4-Cl | CH$_2$CH$_3$ | CH$_3$ | |
| 2.127 | Br | 2-CH$_3$, 4-CH$_3$ | CH$_2$CH$_3$ | CH$_3$ | |
| 2.128 | Br | 2-CH$_3$, 6-CH$_3$ | CH$_2$CH$_3$ | CH$_3$ | |
| 2.129 | Br | 3-CF$_3$ | CH$_2$CH$_3$ | CH$_3$ | |
| 2.130 | Br | 4-CF$_3$ | CH$_2$CH$_3$ | CH$_3$ | |
| 2.131 | Br | 2-F, 4-CF$_3$ | CH$_2$CH$_3$ | CH$_3$ | |
| 2.132 | Br | 2-OCH$_3$, 4-OCH$_3$ | CH$_2$CH$_3$ | CH$_3$ | |
| 2.133 | Br | 2-OCH$_3$-6-OCH$_3$ | CH$_2$CH$_3$ | CH$_3$ | |

USE EXAMPLES

The influence of various representatives of the herbicidal agents, or combinations of herbicide and antidote, according to the invention on the growth of unwanted and crop plants compared with the herbicidal active ingredient alone is illustrated in the following greenhouse experiments.

The vessel employed were plastic flowerpots having a volume of 300 cm$^3$ and filled with a sandy loam containing about 3.0% humus. The seeds of the test plants were sown separately, according to species, and then moistened. The vessels were then covered with transparent plastic hoods until the plants had taken root.

For the postemergence treatment, the plants were grown, depending on growth form, to a height of 3 to 20 cm before being treated with the active ingredients, which were suspended or emulsified in water and sprayed through finely distributing nozzles.

As herbicidal active ingredient, the cyclohexenone derivative X.2 was used in the biological experiments:

$$\text{X.2}$$

with structure containing CH$_3$, H$_5$C$_2$SCHCH$_2$–, OH, =NOC$_2$H$_5$, C$_3$H$_{7n}$, and =O groups on a cyclohexenone ring.

The formulations contain from 0.1 to 95, and preferably from 0.5 to 90, wt % of herbicidal active ingredient and antidote. The application rates of herbicidal active ingredient are from 0.001 to 0.5 kg/ha.

The herbicidal active ingredient x.2 was used (on its own and together with the safener) in the spray liquor as a commercially formulated product (184 g/l EC) together with the same amounts of solvent system XXII given in the table for the safener.

All the safeners were formulated in a mixture consisting of 80% of cyclohexenones and 20% of Emulphor EL (formulation XXII) with 10 wt % of active ingredient.

The vessels were set up in the greenhouse, heat-loving species at from 18° to 35° C. and species from more moderate climates at from 10° to 25° C.

The experiment was run for from 3 to 5 weeks. During this period, the plants were tended and their reactions to the various treatments assessed. Damage by the chemical agents was assessed on a scale from 0 to 100% compared with the untreated control plants, 0 denoting no damage and 100 denoting complete destruction of the plants (*Triticum aestivum*—wheat).

The table below documents the safening action; compound no. 1.001 also greatly improves the tolerance of the cyclohexenone derivative X.2 by crop plants.

TABLE A

Reduction in the damage to wheat caused by the herbicide x.2 as a result of combination with compound 1.001 according to the invention.

| Applic. rate [kg/ha] | | |
|---|---|---|
| Herbicidal act. ingr. x.2 | Safener 1.001 | Damage to wheat in % |
| 0.015 | — | 44 |
| 0.03 | — | 80 |
| 0.015 | 0.06 | 0 |
| 0.03 | 0.125 | 10 |

We claim:

1. A herbicidal composition which comprises a herbicidally/antidotally effective amount of:
at least one 4-aryl-2-haloimidazole-5-carboxylic ester Ia or Ib Ia: structure with phenyl-X$_n$, N, Hal, CO$_2$R$^1$, NH Ib: structure with phenyl-X$_n$, N, Hal, CO$_2$R$^1$, NR$^2$ where
R$^1$ is C$_1$–C$_6$-alkyl, C$_3$–C$_6$-alkenyl or C$_3$–C$_6$-alkynyl,
R$^2$ is C$_1$–C$_6$-alkyl, C$_3$–C$_6$-alkenyl or C$_3$–C$_6$-alkynyl,
Hal is chlorine or bromine,
n is 0 to 3,
X is C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkylsulfinyl, C$_1$–C$_4$-alkylsulfonyl, C$_1$–C$_4$-haloalkylthio, cyano, nitro, carboC$_1$–C$_4$-alkoxy, N,N-di-C$_1$–C$_4$-alkylcarbamoyl or halogen; and with the proviso that in the esters of formula Ia Hal is not bromine when R$^1$ is C$_2$H$_5$ and n is 0, and cyclohexenone derivatives of the formula X IX: structure R$^a$–O–(phenyl)–O–CH(R$^c$)–CO$_2$R$^b$ wherein
R$^d$ is C$_1$–C$_4$-alkyl;
R$^e$ is C$_1$–C$_4$-alkyl, C$_3$–C$_4$-alkenyl, C$_3$–C$_4$-alkynyl or C$_3$–C$_4$-haloalkenyl;
R$^f$ is C$_1$–C$_4$-alkyl which carries one C$_1$–C$_4$-alkylthio or C$_1$–C$_4$-alkoxy radical;
R$^g$ and R$^h$ are hydrogen; and
R$^i$ is hydrogen or an equivalent of an environmentally compatible cation.

2. A herbicidal composition as set forth in claim 1, containing a haloimidazole derivative Ia or Ib and a herbicide of the formula X, the ratio of Ia or Ib:X being from 4:1 to 0.01:1 parts by weight.

3. A process for the selective control of unwanted plant growth, wherein a herbicidally/antidotally effective amount of a haloimidazole derivative of the formula Ia or Ib, or Ia and Ib, as set forth in claim 1 and a cyclohexenone derivative of the formula X as set forth in claim 1 are applied—either simultaneously or one after the other—before, during or after the sowing of the crop plants, or before or during emergence of the crop plants.

4. A process for preventing damage to crop plants by herbicidal cyclohexenone derivatives of the formula X as set forth in claim 1, wherein the seed of the crop plants is treated with a herbicidally/antidotally effective amount of a haloimidazole derivative of the formula Ia or Ib, or Ia and Ib, as set forth in claim 1.

5. A process for the selective control of unwanted plant growth, wherein the leaves of the crop plants and the unwanted plants are treated, either simultaneously or one after the other, with a herbicidally/antidotally effective amount of a haloimidazole derivative of the formula Ia or Ib, or Ia and Ib, as set forth in claim 1 and with a cyclohexenone derivative of the formula X as set forth in claim 1.

6. A process as set forth in claim 3, wherein the crop plants are barley, wheat, Indian corn, sorghum and rice.

7. A process as set forth in claim 4, wherein the crop plants are barley, wheat, Indian corn, sorghum and rice.

8. A process as set forth in claim 5, wherein the crop plants are barley, wheat, Indian corn, sorghum and rice.

9. A herbicidal composition as set forth in claim 1, containing a haloimidazole derivative Ia or Ib and a herbicide of the formula X, the ratio of Ia or Ib:X being from 4:1 to 0.25:1 parts by weight.

10. A process as in claim 3 wherein the application rate of the herbicidal active ingredient is from 0.001 to 0.5 kg/ha and the ratio of the herbicidal active ingredient to antidote is about 1:4 to 1:0.01.

11. A process as in claim 10 wherein the ratio of the herbicidal active ingredient to antidote is about 1:4 to 1:0.25.

* * * * *

UNITED STATES PATENT AND TRADEMARK OFFICE
CERTIFICATE OF CORRECTION

PATENT NO. : 5,211,737
DATED : May 18, 1993
INVENTOR(S) : WRIEDE et al.

It is certified that error appears in the above-identified patent and that said Letters Patent is hereby corrected as shown below:

On the title page, item (54) and in column 1:

In the title, "ARRYL" should be "ARYL".

Column 26:

Claim 1, line 35, delete the formula shown (IX) and insert the correct formula (X) which is in column 2, line 20 of the specification.

Signed and Sealed this

Twenty-first Day of December, 1993

*Attest:*

BRUCE LEHMAN

*Attesting Officer*  Commissioner of Patents and Trademarks